(12) United States Patent
Swanick et al.

(10) Patent No.: US 8,920,483 B2
(45) Date of Patent: Dec. 30, 2014

(54) SURGICAL PROSTHESIS DEPLOYMENT DEVICE

(71) Applicant: Atrium Medical Corporation, Hudson, NH (US)

(72) Inventors: Thomas M. Swanick, Hillsborough, NH (US); Joseph Bienkiewicz, Westford, MA (US)

(73) Assignee: Atrium Medical Corporation, Hudson, NH (US)

( * ) Notice: Subject to any disclaimer, the term of this patent is extended or adjusted under 35 U.S.C. 154(b) by 17 days.

(21) Appl. No.: 13/839,929

(22) Filed: Mar. 15, 2013

(65) Prior Publication Data

US 2013/0331940 A1 Dec. 12, 2013

Related U.S. Application Data

(60) Provisional application No. 61/658,682, filed on Jun. 12, 2012.

(51) Int. Cl.
 *A61F 2/06* (2013.01)
 *A61F 2/00* (2006.01)
(52) U.S. Cl.
 CPC .................................. *A61F 2/0063* (2013.01)
 USPC .......................... 623/1.11; 606/151
(58) Field of Classification Search
 CPC .................. A61F 2/0063; A61F 2/00
 USPC ............ 623/1.11, 23.72, 11.11; 606/139, 151
 See application file for complete search history.

(56) References Cited

U.S. PATENT DOCUMENTS

| 5,147,387 | A | 9/1992 | Jansen et al. |
| 5,263,969 | A | 11/1993 | Phillips et al. |
| 5,304,187 | A | 4/1994 | Green et al. |
| 5,464,403 | A | 11/1995 | Kieturakis et al. |
| 5,503,623 | A | 4/1996 | Tilton, Jr. et al. |
| 5,957,939 | A * | 9/1999 | Heaven et al. ................ 606/151 |
| 6,099,518 | A | 8/2000 | Adams et al. |
| 7,947,054 | B2 | 5/2011 | Eldar et al. |
| 2007/0112361 | A1 | 5/2007 | Schonholz |
| 2007/0196451 | A1 | 8/2007 | Singhal et al. |
| 2009/0125041 | A1 | 5/2009 | Dudai |

FOREIGN PATENT DOCUMENTS

| EP | 0581036 A1 | 2/1994 |
| EP | 2433588 A2 | 3/2012 |
| WO | WO 2004/080348 A1 | 9/2004 |
| WO | WO 2011/128903 | 10/2011 |

OTHER PUBLICATIONS

International Search Report for International Application No. PCT/US2013/044508, dated Sep. 6, 2013.
International Search Report for International Application No. PCT/US2013/044309, dated Sep. 4, 2013.

* cited by examiner

*Primary Examiner* — Victor Nguyen

(57) ABSTRACT

A deployment device, system, and method for deploying a prosthesis. The deployment device includes a housing, a rod disposed within the housing and adapted to rotate relative to the housing, and one or more support members (e.g., bushings, bearings, etc.) rotatably supporting the rod within the housing. An elongate slit is disposed in and entirely through the housing and is positioned in a way that enables the prosthesis to pass therethrough from a loaded, rolled configuration on the rod. The deployment device is generally flexible, e.g., has a bending stiffness of at most about 0.87 N/mm (e.g., about 0.05 N/mm to about 0.87 N/mm). Furthermore, the deployment device enables a user to deploy (e.g., unroll) a prosthesis therefrom at a rate determined manually by the user and in a piece-by-piece fashion.

12 Claims, 9 Drawing Sheets

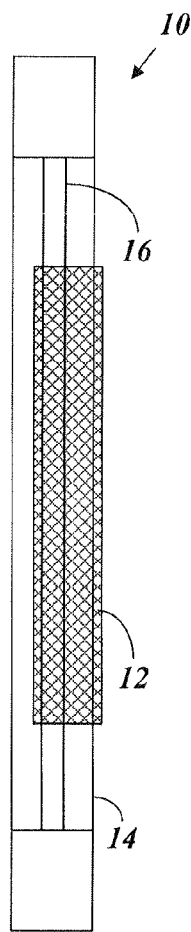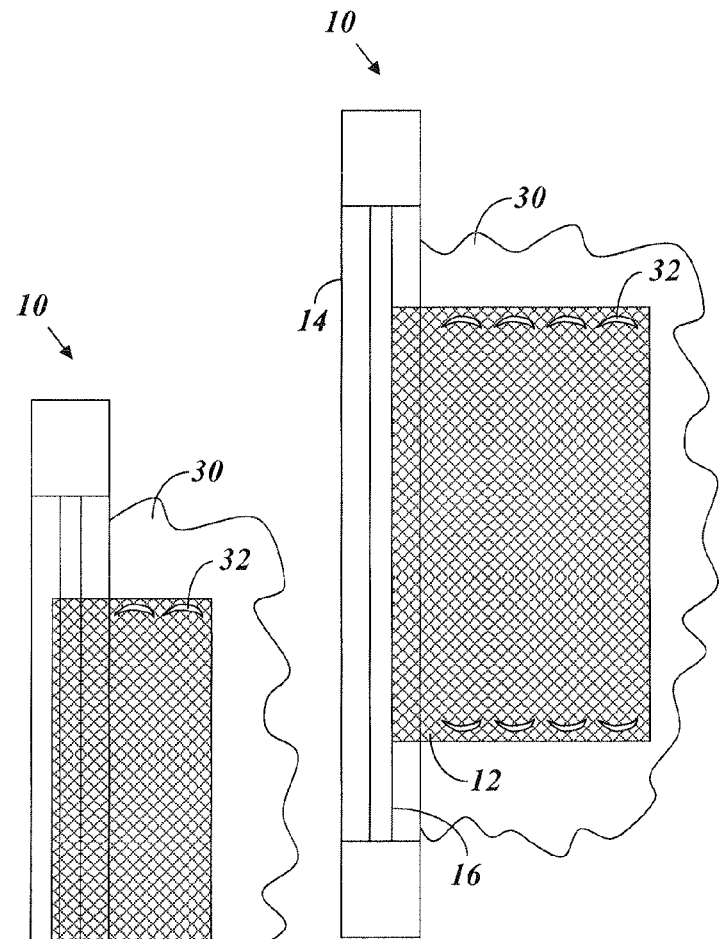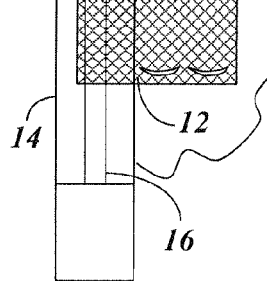
*FIG. 6A*
*FIG. 6B*
*FIG. 6C*

SURGICAL PROSTHESIS DEPLOYMENT DEVICE

RELATED APPLICATION

This application claims priority to, and the benefit of, U.S. Provisional Application No. 61/658,682, filed Jun. 12, 2012, for all subject matter common to both applications. The disclosure of said provisional application is hereby incorporated by reference in its entirety.

FIELD OF THE INVENTION

The present invention relates to surgical prosthesis deployment devices suitable for open and laparoscopic hernia repair. More particularly, the present invention relates to a substantially flexible deployment device capable of releasing and deploying a mesh prosthesis at a variable rate determined manually by a user.

BACKGROUND OF THE INVENTION

In open and laparoscopic hernia repair, mesh prostheses are utilized to provide reinforcement and support at the defect. Such mesh prostheses or other prostheses (e.g., films, surgical fabrics, and the like) are inserted through a small incision cut into the skin and abdomen wall. Generally, such mesh prostheses are flat sheets (e.g., of woven or stitched surgical fabric) that are trimmed to fit the anatomy of the defect site as needed prior to being rolled up and inserted through the incision. Once inserted, the mesh prosthesis is unfolded and affixed to the defect site using sutures or tissue in-growth.

However, manipulating sheet-like prostheses during these procedures presents numerous challenges to a surgeon. For example, trocars, when used, only provide a limited range of motion and require the user to utilize small instruments and graspers to manipulate, unroll, and position the mesh or prosthesis. Moreover, in many instances, the mechanical and physical properties of the sheet-like prostheses change once exposed to bodily conditions and environments (e.g., bodily temperatures, body fluids, etc.). In particular, when exposed to moisture, such sheet-like prostheses can hydrate and become less stiff, making them more prone to rupture or tearing during handling. Furthermore, some of the materials may have a layer of self-adhering material designed to adhere to moist tissue surfaces, which can further complicate a user's ability to handle and place the mesh prosthesis during surgery and implantation.

SUMMARY

Accordingly, there is a need in the art for a prosthesis deployment device that enables the convenient delivery, deployment, and placement of sheet-like prostheses (e.g., meshes, films, patches, fabrics, etc.) during surgical procedures such as hernia repair. The present invention is directed toward further solutions to address this need, in addition to having other desirable characteristics.

In accordance with an example embodiment of the present invention, a prosthesis deployment system is provided. The prosthesis deployment system can include an elongate housing extending along a longitudinal axis. The housing can include an exterior wall surrounding (e.g., and defining) an interior cavity. The housing can have a distal end and a proximal end. An elongate slit opening can be formed in and completely through the exterior wall of the housing to the interior cavity. A rotatable rod can pass through the interior cavity of the housing and can be rotatably coupled to the housing. A prosthesis can be loaded on the rod in a rolled configuration around the rod in such a way that at least a portion of the prosthesis is configured to extend out of the elongate slit opening in the exterior wall of the housing. The prosthesis can be deployed by being pulled through the elongate slit and unrolled from the rod. The deployment system can have a bending stiffness of at most about 0.87 N/mm.

In accordance with further aspects of the present invention, the bending stiffness of the deployment system can be about 0.05 N/mm to about 0.87 N/mm. Rotation of the rod in a loaded configuration can deploy the prosthesis. Rotation of the rod in a loaded configuration can provide deployment of the prosthesis in a segment-by-segment, piecewise manner. The rod in a loaded configuration can rotate at a manually determined rate in either rotational direction relative to the housing. The rod can be completely contained within the housing or partially contained within the housing. The proximal end of the housing can be operationally coupled to a positioning device. The housing and the rod can have substantially the same length. An elongate slot can be formed in the rod enabling the rod to receive the sheet of prosthesis. The elongate slot of the rod can be substantially parallel to the elongate slit opening of the housing.

In accordance with an example embodiment of the present invention, a method of deploying a prosthesis to a target site is provided. The method includes providing a loaded deployment system. The loaded deployment system can include: an elongate housing extending along a longitudinal axis and including an exterior wall surrounding (e.g., defining) an interior cavity, the housing having a distal end and a proximal end; an elongate slit opening formed in and completely through the exterior wall of the housing to the interior cavity; a rotatable rod passing through the interior cavity of the housing and rotatably coupled to the housing; and a prosthesis loaded on the rod in a rolled configuration around the rod in such a way that at least a portion of the prosthesis is configured to extend out of the elongate slit opening in the exterior wall of the housing. The prosthesis can be deployed by being pulled through the elongate slit and unrolled from the rod. The loaded deployment system can have a bending stiffness of at most about 0.87 N/mm. The method further can include positioning the deployment device to the target site and deploying the prosthesis.

In accordance with further aspects of the present invention, positioning the deployment device can include flexing the deployment device in such a way that enables the deployment device to pass through one or more tortuous anatomical passageways. Deploying the prosthesis further can include (a) rolling the rod in such a way that a first portion of the prosthesis is deployed from the housing and exposed to the target site; (b) affixing the first exposed portion to the target site; (c) subsequent to affixing the first portion to the target site, rolling the rod in such a way that a second portion of the prosthesis deploys from the housing and is exposed to the target site; and (d) affixing the second exposed portion to the target site.

In accordance with an example embodiment of the present invention, a method of deploying a prosthesis to a target site is provided. The method can include providing a deployment device. The deployment device can include an elongate housing extending along a longitudinal axis and including an exterior wall surrounding (e.g., defining) an interior cavity. The housing can have a distal end and a proximal end. The deployment device can include an elongate slit opening formed in and completely through the exterior wall of the housing to the interior cavity. The deployment device can include a rotatable rod passing through the interior cavity of the housing and rotatably coupled to the housing. The method further can include providing the prosthesis and loading the deployment device with the prosthesis in such a way that the prosthesis is rolled around the rod and at least a portion of the prosthesis extends out of the elongate slit opening in the exterior wall of the housing, forming a loaded deployment system. The loaded deployment system can have a bending stiffness of about of at most about 0.87 N/mm. The method further can include positioning the loaded deployment system to the target site and deploying the prosthesis by pulling the prosthesis through the elongate slit and unrolling the prosthesis from the rod.

In accordance with further aspects of the present invention, positioning the loaded deployment system can include flexing the loaded deployment system in such a way that enables the loaded deployment system to pass through one or more tortuous anatomical passageways. Deploying the prosthesis can include (a) rolling the rod in such a way that a first portion of the prosthesis deploys from the housing and is exposed to the target site; (b) affixing the first exposed portion to the target site; (c) subsequent to affixing the first portion to the target site, rolling the rod in such a way that a second portion of the prosthesis deploys from the housing and is exposed to the target site; and (d) affixing the second exposed portion to the target site.

In accordance with an example embodiment of the present invention, a prosthesis deployment kit can include a prosthesis and a deployment device. The deployment device can include an elongate housing extending along a longitudinal axis and comprising an exterior wall surrounding (e.g., defining) an interior cavity. The housing can have a distal end and a proximal end. An elongate slit opening can be formed in and completely through the exterior wall of the housing to the interior cavity. The elongate slit opening can be substantially parallel to the longitudinal axis of the housing and can extend between the distal end and the proximal end. A rotatable rod can pass through the interior cavity of the housing and can be rotatably coupled to the housing. The prosthesis can be deployed from a rolled configuration on the rod by being pulled through the elongate slit and unrolled from the rod. The deployment device can have a bending stiffness of at most about 0.87 N/mm when the prosthesis is loaded on the rod in the rolled configuration.

BRIEF DESCRIPTION OF THE FIGURES

These and other characteristics of the present invention will be more fully understood by reference to the following detailed description in conjunction with the attached drawings, in which:

FIG. 6A through 6C are top views of examples of various progressive stages of deploying a mesh prosthesis utilizing a deployment device according to an example embodiment of the present invention;

DETAILED DESCRIPTION

Figure 1A:
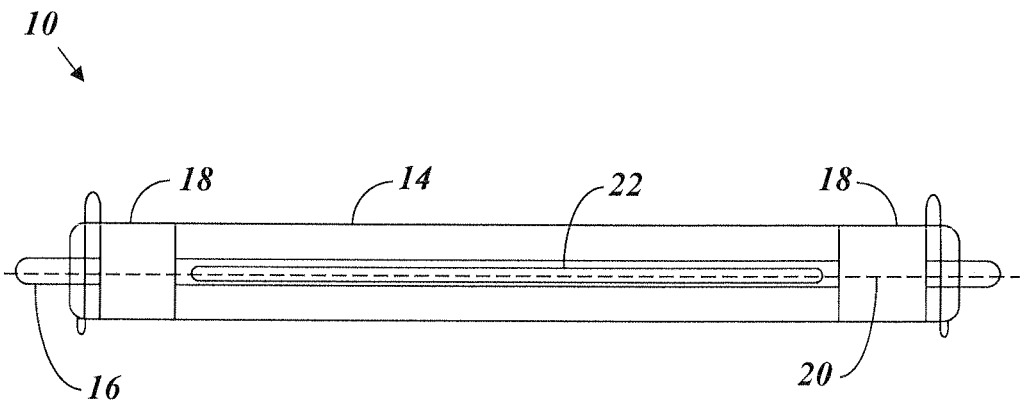
FIG. 1A is a front view of a deployment device according to an example embodiment of the present invention.

An illustrative embodiment of the present invention relates to a deployment device for deploying a prosthesis, such as a mesh prosthesis. The deployment device includes a housing, a rod disposed within the housing and adapted to rotate relative to the housing, and one or more support members (e.g., bushings, bearings, etc.) rotatably supporting the rod within the housing. An elongate slit is disposed in and through the housing and is generally aligned with and offset from a longitudinal axis of the rod in a manner enabling the prosthesis to pass therethrough from a loaded, to rolled configuration on the rod.

Notably, the deployment device is generally flexible and is sufficiently flexible to bend or otherwise flex in a manner suitable for navigating tortuous anatomical passageways during delivery of the device to a targeted deployment location. For example, in illustrative embodiments of the present invention, the deployment device has a bending stiffness of at most about 0.87 N/mm (and in illustrative implementations described herein generally between about 0.05 N/mm to about 0.87 N/mm). Furthermore, the deployment device is adapted to allow a user to deploy (e.g., unroll) a mesh prosthesis therefrom at a rate determined manually by the user. Accordingly, the user is enabled to utilize a manual variable deployment rate when releasing the prosthesis from the deployment device. Beneficially, this allows the user to affix the prosthesis to the bodily tissue in portions. More specifically, the user is enabled to unroll a portion of the prosthesis, affix the unrolled portion, and subsequently continue in this pattern of unrolling and affixing additional portions of the prosthesis until deployment is completed.

FIGS. 1A through 9, wherein like parts are designated by like reference numerals throughout, illustrate example embodiments of a prosthesis deployment device, according to the present invention. Although the present invention will be described with reference to the example embodiments illustrated in the figures, it should be understood that many alternative forms can embody the present invention. One of skill in the art will additionally appreciate different ways to alter the parameters of the embodiments disclosed, such as the size, shape, or type of elements or materials, in a manner still in keeping with the spirit and scope of the present invention.

Figure 1B:
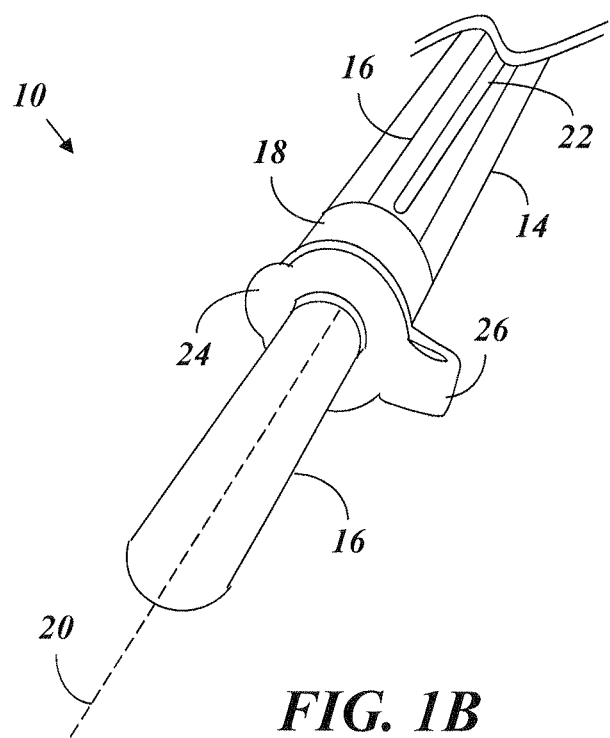
FIG. 1B is a perspective view of the deployment device of FIG. 1A, according to aspects of the present invention.

FIG. 1A illustrates a front view of a deployment device 10 configured to deploy a mesh prosthesis 12 according to an example embodiment of the present invention. FIG. 1B further depicts an end of the deployment device 10 of FIG. 1A from a perspective view. As illustrated, the deployment device 10 generally includes a housing 14, a rod 16, and one or more support members 18 (e.g., bushings, bearings, and the like) supporting the rod 16. In the example embodiment of FIGS. 1A and 1B, the housing 14 includes a generally tubular (e.g., cylindrical shaped) exterior wall surrounding an interior cavity, in which the rod 16 is disposed. The support members 18 are located at the ends of the housing 14 and maintain the rod 16 in substantially fixed Cartesian coordinate positions (x, y, and z positions) relative to the housing 14, while also enabling the rod 16 to rotate independently of (e.g., relative to) the housing 14. The rod 16 has a longitudinal axis 20, about which it rotates when so actuated. The rod 16 can be enabled to rotate in both rotational directions (e.g., both clockwise and counter-clockwise) about its longitudinal axis 20 relative to the housing 14. Alternatively, the rod 16 can be restricted in its rotational motion such that it is only adapted to rotate in a single direction.

As depicted herein, the housing 14 is formed of a substantially clear and transparent material, in part to provide an interior view of the rod 16 and the mesh prosthesis 12 when loaded thereon. However, one of skill in the art will appreciate that the housing 14 alternatively can be formed of tinted, translucent, opaque, colored, and other types of materials partially or wholly blocking such an interior view. The housing 14 according to embodiments of the present invention is not limited to a specific type of material or color/degree of transparency. Rather, any suitable material(s) can be utilized.

The housing 14 also includes an elongate slit 22 disposed therein and entirely therethrough. Stated differently, the elongate slit 22 is an opening that leads from the) interior cavity of the housing 14 to an environment external to the deployment device 10. The elongate slit 22 is generally sized, dimensioned, and positioned to enable the mesh prosthesis 12 to slide therethrough from a loaded position on the rod 16. For example, the elongate slit 22 can be adapted such that when the mesh prosthesis 12 is loaded by being wrapped around the rod 16, the mesh prosthesis 12 is enabled to be deployed from the deployment device 10 by passing through the elongate slit 22. Accordingly, the elongate slit 22 can have a length that is equal to or greater than a dimension of the mesh prosthesis 12 along the longitudinal axis of the rod 16 when appropriately loaded on the rod 16. In the example embodiment of FIGS. 1A and 1B, the elongate slit 22 additionally has a longitudinal axis (not shown) that is substantially parallel to the longitudinal axis 20 of the rod 16.

The deployment device 10 optionally can include an end cap 24 disposed at each end of the housing 14. The end caps 24 can include two O-ring members coupled together by a hinge 26, as depicted in FIGS. 1A and 1B. The end caps 24 can provide additional support in fixing the Cartesian coordinate positions (x, y, and z positions) of the rod 16, e.g., by forming a tight fit around the rod 16. In some alternative embodiments, the end caps 24 are included in the deployment device, but do not include the hinge 26. In such alternative embodiments, the end caps 24 can include only a single O-ring member or two (or more) O-ring members coupled together by a non-pivotal mechanism. Furthermore, in yet other embodiments according to the present invention, the end caps 24 (e.g., on the hinge 26) are not included in the deployment device 10. Accordingly, it should be appreciated that the end caps 24 and/or the hinge 26 are optional and need not be included in the deployment device 10 in all embodiments of the present invention.

Figure 2A:
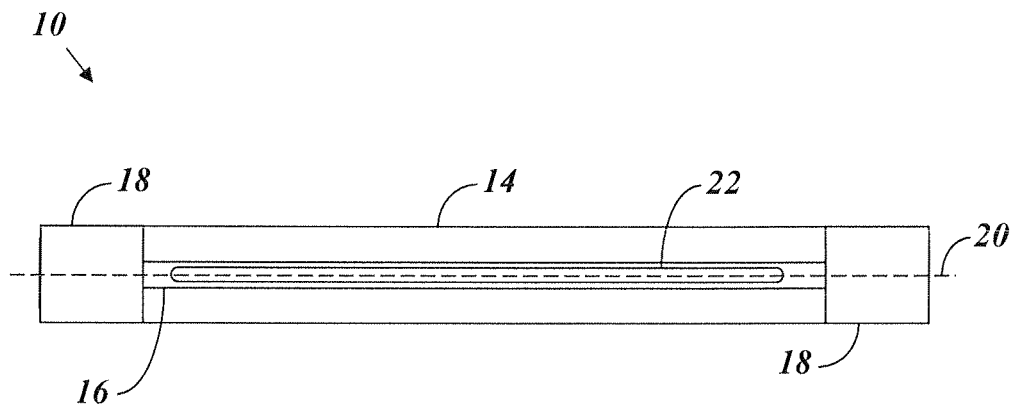
FIG. 2A is a front view of a deployment device according to an example embodiment of the present invention.
Figure 2B:
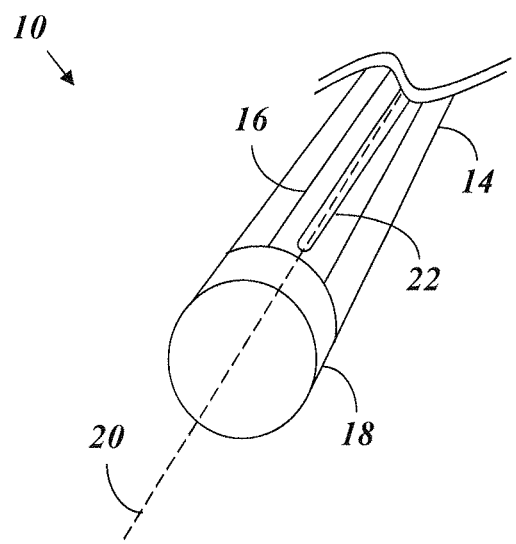
FIG. 2B is a perspective view of the deployment device of FIG. 2A, according to aspects of the present invention.

In the example embodiment of FIG. 1, the rod 16 is disposed in the housing 14, but also extends beyond each end of the housing 14. In other embodiments, however, the rod 16 is contained and disposed entirely within the housing 14. FIGS. 2A and 2B illustrate one such example embodiment of the deployment device 10, in which the rod 16 is entirely contained within the housing 14. FIG. 2A depicts the deployment device 10 from a front view, and FIG. 2B depicts an end of the deployment device 10 from a perspective view. In the example embodiment of FIGS. 2A and 2B, the rod 16 has a length that is substantially equal to or slightly less the length of the housing 14.

Figure 3:
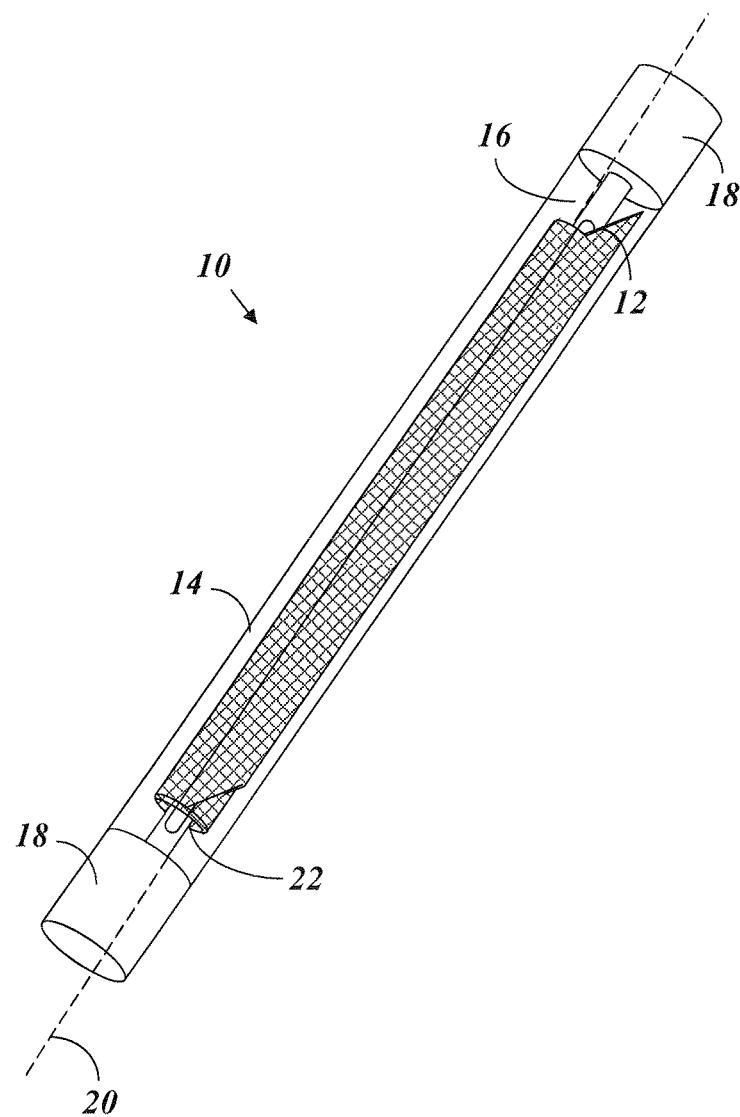
FIG. 3 is a perspective view of the deployment device of FIGS. 2A and 2B loaded with a mesh prosthesis, according to aspects of the present invention.

Referring now to FIG. 3, the deployment device 10 of FIGS. 2A and 2B is depicted, further including the mesh prosthesis 12 loaded therein. As shown from the perspective view of FIG. 3, the mesh prosthesis 12 is wound around, or rolled onto, the rod 16 and forms one or more revolutions around the rod 16. In the configuration depicted in FIG. 3, the mesh prosthesis 12 is slightly exposed and extends through the elongate slit 22, e.g., at least in an amount sufficient to enable a user to grip and pull the mesh prosthesis 12 therethrough, for purposes of deploying the mesh prosthesis 12.

Figure 4:
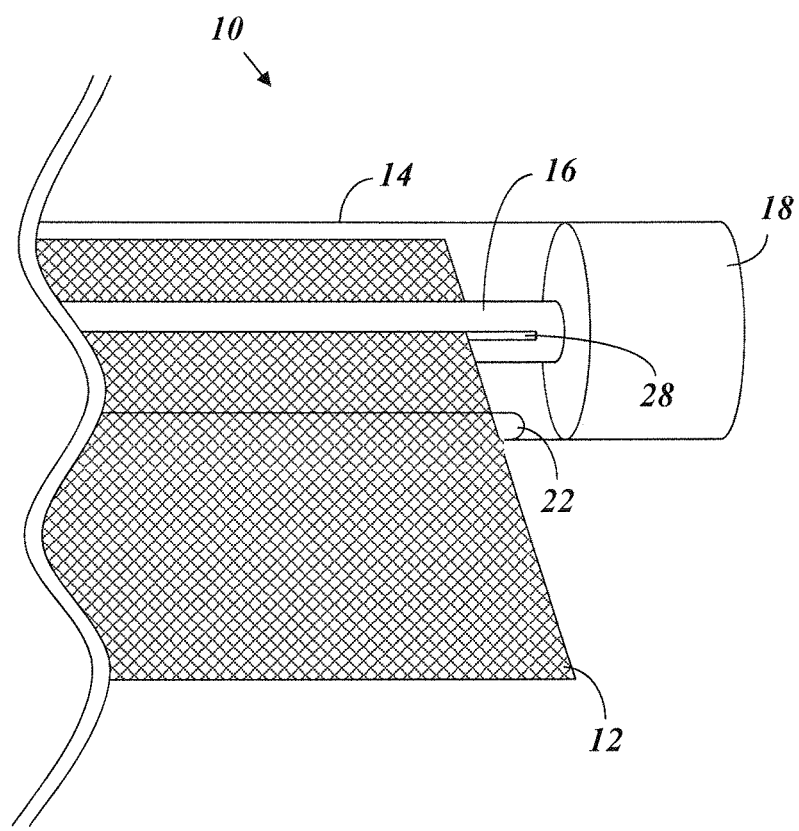
FIG. 4 is a perspective view of a side of a deployment device at one end according to an example embodiment of the present invention.

The mesh prosthesis 12 can be loaded in the deployment device 10 in any number of suitable ways. For example, as depicted in FIG. 3, the mesh prosthesis 12 generally may be wound around or otherwise rolled around the rod 16. The mesh prosthesis 12 can be coupled (e.g., detachably coupled) to the rod 16. For example, as depicted in FIG. 4, the rod 16 can be a split rod that includes a thin slot 28 within which the mesh prosthesis 12 is capable of being held in place (e.g., detachably or non-detachably), and which is thereby configured to affix the mesh prosthesis 12 to the rod 16. For example, the thin slot 28 can be sufficiently thin to apply an amount of pressure suitable for frictionally holding the mesh prosthesis 12 in place in the absence of a tugging or other removal force applied by a user on the mesh prosthesis 12. In the example embodiment of FIG. 4, the thin slot 28 in the rod 16 extends entirely through a width of the rod 16 (e.g., along a diameter of the rod 16), and extends along a majority of the length of the rod 16. The thin slot 28 can have a longitudinal axis (not shown) that is substantially parallel to that of the rod 16 and/or the elongate slit 22.

Upon reading the present specification, one of skill in the art will appreciate a variety of other ways for coupling (detachably or non-detachably) the mesh prosthesis 12 to the rod 16. All such modifications and alternatives are contemplated within the) scope of the present invention. The present invention is not limited to the illustrative examples provided herein and depicted in the figures. Any suitable mechanism for coupling or otherwise joining the mesh prosthesis 12 with the rod 16 can be used in the embodiments described herein.

During operation, the deployment device 10 is loaded with the mesh prosthesis 12 (either at a remote manufacturing facility, or on site at the medical facility where the mesh prosthesis 12 will ultimately be deployed), inserted through an incision, and advanced to the defect site, e.g., using one or more trocars. The flexibility of the loaded deployment device 10 enables the device to bend around obstacles as it is moved into position. Upon reaching the defect site, a small exposed portion of the mesh prosthesis 12 extending from the elongate slit 22 is gripped by the user (e.g., using graspers or other suitable instruments) and pulled outward away from the deployment device 10. This causes the rod 16 to rotate about its longitudinal axis 20, thereby unrolling the mesh prosthesis 12 and causing the mesh prosthesis 12 to be removed from the housing 14 through the elongate slit 22.

Figure 5:
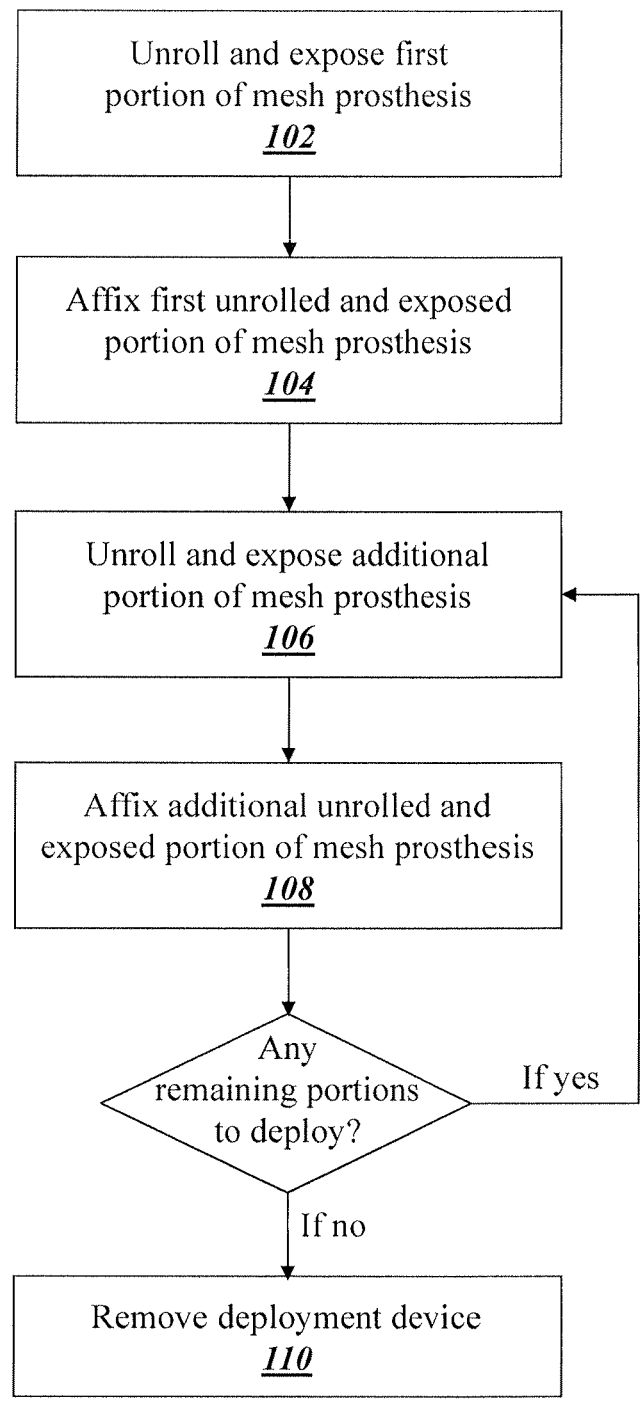
FIG. 5 is a flowchart depicting an example of a method for deploying a mesh prosthesis using a deployment device according to an example embodiment of the present invention.

Notably, the deployment device 10 enables the user to deploy and unroll the mesh prosthesis 12 manually in discrete sections or portions, e.g., in a piecewise or step-by-step fashion. This allows the user to unroll and affix the mesh prosthesis 12 in discrete portions. For example, FIG. 5 depicts a method for using the deployment device 10 to deploy the mesh prosthesis 12, in accordance with an example embodiment of the present invention. A user can unroll and expose a first portion of the mesh prosthesis 12 (step 102), and simultaneously or subsequently affix the unrolled and exposed portion of the deployment device 10 (step 104). This pattern of unrolling and affixing can be generally repeated for additional (e.g., remaining) portions of the mesh prosthesis 12 until deployment is completed. For example, it is assumed in FIG. 5 that is at least one additional portion of the mesh prosthesis 12 that is to be affixed to provide adequate support to the defect site. Accordingly, the additional portion can be unrolled and exposed (step 106). Simultaneously or subsequently with step 106, the additional unrolled and exposed portion can be affixed by the user (step 108). If additional portions of the mesh prosthesis 12 must be deployed and affixed, then steps 106 and 108 can be repeated for each remaining portion. Once the final remaining portion of the mesh prosthesis 12 has been deployed and affixed, the user removes the deployment device 10 (and any unused portions of the mesh prosthesis 12 remaining therein) from the body of the patient (step 110). The procedure then can be completed, as would be appreciated by one of skill in the art. As will be described in greater detail herein, the final portion of the mesh prosthesis 12 that is deployed from the deployment device 10 and affixed by the user can either be (a) the last remaining portion of the mesh prosthesis 12 contained within the deployment device 10 (in which case the mesh prosthesis 12 is detachably removed from the rod 16 during the final iteration of step 108) or can be (b) detached (e.g., by cutting with surgical scissors) from an excess portion of mesh prosthesis 12 which remains coupled to the deployment device 10 and is removed in step 110.

This procedure of stepwise deployment and fixation of the mesh prosthesis 12 in discrete portions, as depicted in the example embodiment of FIG. 5, enables a user to manually deploy (e.g., unroll and expose) the mesh prosthesis 12 from the deployment device 10 at his or her own pace. This assists in preventing the mesh prosthesis 12 from being deployed in excess amounts that typically produce undesired folds, etc. in the mesh prosthesis 12. Stated differently, the user can manually control the amount of slack in the mesh prosthesis 12 during deployment, which allows the user to avoid the formation of folds, the premature adhesion at incorrect locations, and other complications associated with the existing devices presently used in the art for deployment such a mesh prosthesis 12.

For example, FIGS. 6A through 6C depict various stages of the mesh prosthesis 12 being deployed from the deployment device 10. In the top views presented in FIGS. 6A through 6C, the elongate slit 22 is not visible due to the orientation of the deployment device 10. However, in FIGS. 6A through 6C (relative to the page), the elongate slit 22 is positioned along the right-hand side of the housing 14.

As depicted in FIG. 6A, only a small portion of the mesh prosthesis 12 (e.g., the smaller portion of the mesh prosthesis 12 graspable by a user) extends through the elongate slit 22 in the housing 14. In FIG. 6B, approximately half of the mesh prosthesis 12 has been deployed from the deployment device 10 and affixed with surgical sutures 32 to bodily tissue 30 at the defect site in the patient. In FIG. 6C, almost all of the mesh prosthesis 12 has been deployed from the deployment device 10 and affixed with the surgical sutures 32 to the bodily tissue 30 at the defect site. As is demonstrated by FIGS. 6A through 6C, in each instance of unrolling some portion of the mesh prosthesis 12, the user is enabled to pause in deploying the mesh prosthesis 12, then affix any newly exposed and unaffixed portion of the mesh prosthesis 12, and subsequently resume with deployment (e.g., unrolling) the mesh prosthesis 12.

In addition to affixing the mesh prosthesis 12 with the surgical sutures 32, the mesh prosthesis 12 can additionally or alternatively be affixed using any other suitable method, as would be appreciated by one of skill in the art upon reading the present specification. For example, in embodiments where the mesh prosthesis 12 includes an adhering layer adapted to "stick" with the bodily tissue 30, the mesh prosthesis 12 can be affixed simply by being placed in contact with the bodily tissue 30. Any suitable fixation mechanism is contemplated within the scope of the present invention. Furthermore, the method for affixing the mesh prosthesis 12 can be selected based on the properties of the mesh prosthesis 12 (e.g., tissue ingrowth, etc.), as would be appreciated by one of skill in the art upon reading the present specification.

As described previously herein, the mesh prosthesis 12 can be detachably coupled to the rod 16 such that the entire mesh prosthesis 12 is deployed from the deployment device 10 and affixed by the user, e.g., to the abdomen wall or other bodily tissue. In such embodiments according to the present invention, the user can detachably remove the mesh prosthesis 12 from the rod 16 by slightly tugging or gently pulling on the mesh prosthesis 12. The mesh prosthesis 12 can be detachably coupled to the rod 16 in such a way that the force required to remove the mesh prosthesis 12 is less than the force required to produce a tear or rip in the mesh prosthesis 12, as would be appreciated by one of skill in the art upon reading the present specification.

However, in accordance with alternative embodiments of the present invention, the mesh prosthesis 12 is loaded into the deployment device 10 in an amount that is greater than the amount required for the particular procedure. Stated differently, excess amounts of the mesh prosthesis 12 can be included in the deployment device 10, thereby enabling the user to make a cut (e.g., using surgical scissors) in the mesh prosthesis 12 (e.g., at a location on a portion of the mesh prosthesis 12 positioned outside of the housing 14) once a suitable amount of the mesh prosthesis 12 has been deployed. In such alternative embodiments, the mesh prosthesis 12 can be detachably coupled to the rod 16 (as described previously herein), or can be non-detachably coupled to the rod 16 (e.g., permanently adhered or affixed to the rod 16, etc.). One of skill in the art will appreciate yet other ways to affix, couple, or otherwise adjoin the mesh prosthesis 12 with the rod 16 upon reading the present specification. All such alternatives and modifications are contemplated by the present invention. The mesh prosthesis 12 and the rod 16 can be adjoined in any suitable manner.

The rod 16 can be a cylindrical rod and can be coaxial with the housing 14, as depicted in the example embodiments of FIGS. 1A through 4. In other embodiments, however, the rod 16 and the housing 14 are not coaxial. Furthermore, the rod 16, the housing 14, or both can be non-cylindrical. In such embodiments, the rod 16, the housing 14, or both instead assume other shapes, e.g., polygonal, etc. One of skill in the art will appreciate a wide variety of ways to modify the shape, position, and the like, of the rod 16 and/or the housing 14 upon reading the present specification. All such modifications and alternatives are contemplated within the scope of the present invention. In the example embodiments of FIGS. 1A through 4, the housing 14 and the rod 16 are sized such that there is at least a small amount of space between the housing 14 and the outermost revolution of the mesh prosthesis 12 when the deployment device 10 is loaded with the mesh prosthesis 12.

In the example embodiments of FIGS. 1A through 4, the elongate slit 22 is generally centered along the length of the housing 14. Accordingly, when the mesh prosthesis 12 is loaded onto the rod 16, the mesh prosthesis 12 can be centered along the length of the rod 16, thereby enabling the mesh prosthesis 12 to be removed through the elongate slit 22 during deployment, as previously described herein. The mesh prosthesis 12 can be loaded in the deployment device 10 in any number of suitable ways. For example, the mesh prosthesis 12 can be rolled around the rod 16 prior to insertion of the rod 16 into the housing 14, and then the rod 16 with the mesh prosthesis 12 rolled therearound can be inserted into the housing 14 to result in the loaded deployment device 10, e.g., as depicted in the example embodiment of FIG. 3. However, the mesh prosthesis 12 can be rolled or wound around the rod 16 in any number of suitable ways ensuring proper preservation of the mesh prosthesis 12, e.g., using one or more mechanical devices to guide the mesh prosthesis 12 around the rod 16, etc.

In general, the component parts of the deployment device 10 described herein can be formed of any suitable biocompatible materials. In illustrative embodiments, the deployment device 10 is substantially more flexible than conventional devices presently utilized in the art. For example, in one embodiment, the rod 16 is a solid rod, e.g., formed of a suitable flexible material, such as any medical grade plastic or any other suitable material. For example, the housing 14 and the rod 16 both can be formed of a copolyester, e.g., Eastar™ Copolyester 6763 manufactured by Eastman Chemical Company (headquartered in Kingsport, Tenn.). The support members 18 can be bushings formed of any plastic having a low coefficient of friction (e.g., potentially including sealing plastic), or of any other suitable material.

Example 1

A first example of the deployment device 10 was analyzed using a computerized simulation. In particular, a finite elements method was used to analytically assess the bending stiffness of the deployment device 10 (without the mesh prosthesis 12 rolled around the rod 16). The finite elements method was also used to analytically assess the bending stiffness of the housing 14 alone. In the first example, the housing 14 had a length of about 101.6 mm, an outer diameter of about 5 mm, and a thickness of about 0.254 mm. The elongate slit 22 in the housing 14 had a length of about 90% of the length of the housing 14, i.e., about 91.4 mm and a width of about 2 mm Faster™ Copolyester 6763 (of which the housing 14 and the rod 16 were formed in the first example) has a flexural modulus of about $3 \times 10^5$ PSI, a tensile modulus of about $3 \times 10^5$ PSI, a tensile stress at yield of about 7300 PSI, a tensile stress at break of about 4100 PSI, and a flexural yield strength of about 10200 PSI.

As stated previously herein, in the first example, bending stiffness was analyzed for the deployment device 10 (in the absence of the mesh prosthesis 12), and also for the housing 14 alone (i.e., in the absence of other components of the deployment device 10). The 5 mm outer diameter housing 14 alone (with the elongate slit 22 disposed therein and no other components of the deployment device 10 included therein) was found to have a bending stiffness of about 0.050 N/mm. This value of bending stiffness (and all subsequent values of bending stiffness described herein and expressed herein in terms of N/mm) is an expression of reaction force of the housing 14 generated in response to an amount of displacement produced at an end of the housing 14 by displacing that end away from the longitudinal axis 20 of the housing 14 while holding the opposite end fixed. Specifically, the bending stiffness is quantified as the reaction force per unit displacement.

In all bending stiffness simulation tests, the bending stiffness was analyzed by simulating a first displacement in an end of the deployment device 10 (or in an end of the housing 14 alone) while assuming that the opposite end is fixed, and calculating the reaction force produced in response to the first displacement. These displacement simulations of the deployment device 10 (and the housing 14 alone) were repeated for a plurality of different displacement values. The calculations of the reaction force produced in response to the displacement were performed using numerical analysis. Specifically, a final displacement value was specified in the simulation, and the analysis time-stepping algorithm provided converged solutions at intermediate displacements. The resulting data set (including the intermediate displacements) was graphed as reaction force versus displacement. The final value of bending stiffness was achieved by performing linear regression analysis on the data set.

In addition to analyzing the bending stiffness of the housing 14 alone using the computer simulation, the bending stiffness of the deployment device 10 was also analyzed using the computer simulation (in the same manner as described previously herein). In all computer simulations in which the bending stiffness of the deployment device 10 was considered, the deployment device 10 was considered in absence of the mesh prosthesis 12. However, upon reading the present specification, it would be appreciated by one of skill in the art that the bending stiffness of the mesh prosthesis 12 (e.g., even when in the rolled configuration) generally will be less (e.g., significantly less) than that of the deployment device 10. Accordingly, in such cases where the mesh prosthesis 12 has bending stiffness that is significantly less than the bending stiffness of the deployment device 10, the mesh prosthesis 12 will not contribute substantially to the bending stiffness of the deployment device 10 (e.g., even when the mesh prosthesis 12 is loaded on the rod 16 in the rolled configuration). Thus, in such situations contemplated herein, the bending stiffness of the deployment device 10 will be substantially the same regardless of whether the mesh prosthesis 12 is included in the deployment device 10 (e.g., loaded on the rod 16 in a rolled configuration). Stated differently, in illustrative embodiments of the present invention, the bending stiffness of the deployment device 10 (e.g., as measured in the manner described herein) with the mesh prosthesis 12 loaded on the rod 16 in a rolled configuration is substantially the same as the bending stiffness of the deployment device 10 when the mesh prosthesis 12 is not loaded on the rod 16 of the deployment device 10 and not included in the deployment device 10.

Figure 7:
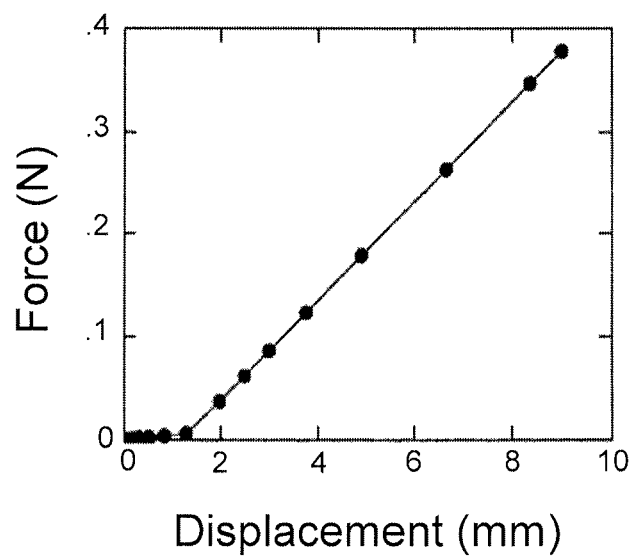
FIG. 7 is a graph of bending stiffness data measured for a first example of a deployment device that was analyzed using a computer simulation, according to aspects of the present invention.
Figure 8:
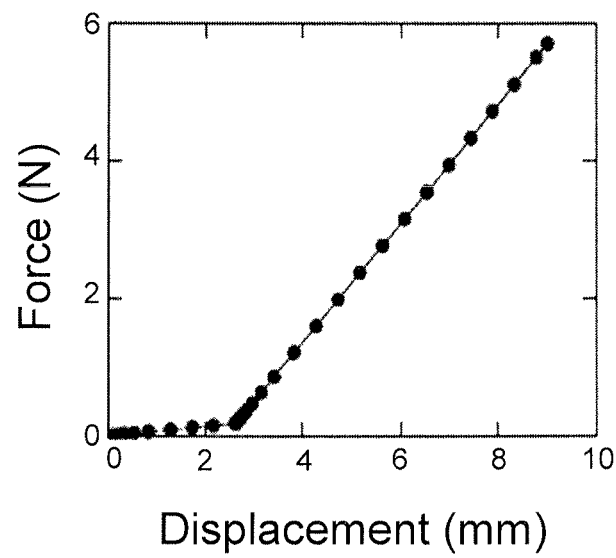
FIG. 8 is a graph of bending stiffness data measured for a second example of a deployment device that was analyzed using a computer simulation, according to aspects of the present invention.

In the first example, the deployment device 10 was assumed to include the 5 mm outer diameter housing 14 previously described herein, and the rod was assumed to be a solid rod formed of Easter™ Copolyester 6763 having an outer diameter of about 2 mm. When tested for bending stiffness using the computer simulation, the simulated deployment device 10 generated the bending stiffness data presented in the graph of FIG. 7. Accordingly, as with the bending stiffness simulation tests performed on the housing 14 alone, the bending stiffness data presented in the graph of FIG. 7 represents a plurality of calculations of reaction force in the housing 14 generated in response to a particular amount of displacement produced at an end of the housing 14 by bending that end away from the longitudinal axis 20 of the housing 14 while holding the opposite end fixed. As shown in the graph of FIG. 7, the deployment device 10 exhibited an initial phase of lower bending stiffness, after which the deployment device 10 exhibited a higher bending stiffness of about 0.049 N/mm. It is contemplated that the initial phase of lower bending stiffness in the deployment device 10 corresponds to an amount of bending that resulted in only the housing 14 and not the rod 16 being bent, whereas the later phase of higher bending stiffness in the deployment device 10 corresponds to an amount of bending that resulted in both the housing 14 and the rod 16 being bent.

Example 2

In a second example, the deployment device 10 was analyzed for bending stiffness using the computer simulation described previously herein with reference to the first example. As with the first example, both the deployment device 10 (in absence of the mesh prosthesis 12) and the housing 14 alone were tested for bending stiffness using the computer simulation. In the second example, the housing 14 had a length of about 101.6 mm, an outer diameter of about 10 mm, and a thickness of about 0.508 mm. In the second example, the elongate slit 22 possessed the same dimensions as in the first example, i.e., a length of about 91.4 mm and a width of about 2 mm. The housing 14 was assumed to be constructed of the same material (Easter™ Copolyester 6763). In this second example, the housing 14 alone (with no other components of the deployment device 10 included therein) exhibited a bending stiffness of about 0.919 N/mm (as measured in the manner described previously herein). In the second example, the deployment device 10 was assumed to include the 10 mm outer diameter housing 14 described previously herein, and the rod 16 was assumed to be a solid rod formed of Easter™ Copolyester 6763 and having an outer diameter of about 4 mm. When tested for bending stiffness using the computer simulation, the simulated deployment device 10 of the second example generated the data set presented in the graph of FIG. 8. As depicted, subsequent to an initial phase of lower bending stiffness exhibited during the first roughly 2.5 mm of displacement during which the rod 16 did not bend, the deployment device 10 of the second example exhibited a bending stiffness of about 0.869 N/mm (as quantified in the manner described previously herein).

In accordance with some embodiments of the present invention, the mesh prosthesis 12 can be constructed, sealed, packaged, and sold as a single pre-loaded unit, thereby providing more efficient packaging and greater ease of use by removing to the step of the user loading the deployment device 10 with the mesh prosthesis 12. The deployment device 10 generally can be used on a one-time basis (e.g., can be designed to be disposed of after a single use), or can be adapted to be used repeatedly for multiple operations (e.g., with requisite cleaning, sterilizing, and the like between successive uses).

In accordance with certain illustrative embodiments of the present invention, the deployment device 10 does not include springs, tensioners, or other mechanical and/or electrical components/devices producing a restoring force or torque on the rod 16 for causing the rod 16 to automatically deploy (e.g., unspool) the mesh prosthesis 12 once positioned at the defect site. Rather, in such illustrative embodiments of the present invention, the deployment device 10 is adapted to enable a user to deploy the mesh prosthesis 12 at his or own manually determined rate, as previously described herein. This enables the user to utilize a variable rate, e.g., to halt deployment of the mesh prosthesis 12 for the purpose of affixing the mesh prosthesis 12 in portions. Furthermore, in accordance with certain illustrative embodiments of the present invention, multiple tubular members (e.g., multiple tubes adapted to slide relative to one another) are not included for implementing such automatic spring-loaded release of the mesh prosthesis 12. Rather, in certain illustrative embodiments of the present invention, only the housing 14 (e.g., implemented as a single tubular member) is included in the deployment device 10.

Notably, no conventional device for deployment of a surgical fabric possesses a bending stiffness of about 0.87 N/mm or less (e.g., about 0.05 N/mm to about 0.87 N/mm). One of skill in the art will appreciate that this value of bending stiffness represents a substantial decrease over the bending stiffness of conventional devices. Conventional devices generally fail to recognize or teach the value in providing a device (such as the deployment device 10) that is enabled to reversibly flex to overcome triangulation limitations with traditional non-articulating devices (e.g., graspers, etc.) and to better navigate tortuous passageways (e.g., intraperitoneal passageways) when advancing toward a defect site (e.g., the site of a hernia). Conventional devices strive to preserve rigidity to prevent the formation of bends or kinks in the mesh prosthesis 12 when advancing the mesh prosthesis 12 toward the defect site. Accordingly, the deployment device 10 according to embodiments of the present invention improves upon conventional devices in providing a device that is sufficiently flexible to bend and flex while traveling through tortuous body lumens in the manner described herein.

It should be appreciated that the values of bending stiffness produced in the simulation of the first example and the second example are illustrative and depend on a wide variety of factors (e.g., size, shape, materials, and the like), which may be changed or altered depending on the particular implementation and intended application. All such alterations and modifications are contemplated within the scope of the present invention. For example, in some embodiments a housing 14 having an outer diameter of about 3 mm is utilized, which may produce a deployment device 10 having a bending stiffness of less than about 0.05 N/mm. Furthermore, adjustments to shape and/or materials for the deployment device 10 of the second example may produce a deployment device 10 having a bending stiffness of greater than about 0.87 N/mm. Accordingly, the values provided herein are illustrative and in no way limit the present invention. The deployment device 10 generally may have any suitable value of bending stiffness, provided that the deployment device 10 has a bending stiffness sufficient to enable the deployment device 10 to suitably flex to navigate the particular intended bodily passageways (e.g., intraperitoneal passageways in the case of hernia repair), as previously described here.

In accordance with further aspects, the deployment device 10 according to embodiments of the present invention deploys the mesh prosthesis 12 from a protective housing (e.g., such as the housing 14) at a manually determined rate or in a piecewise fashion conducive for repeated unrolling and fixation of discrete portions of the mesh prosthesis 12. Such manually determined rates provide for greater accuracy and control over the deployment relative to conventional devices.

Figure 9:
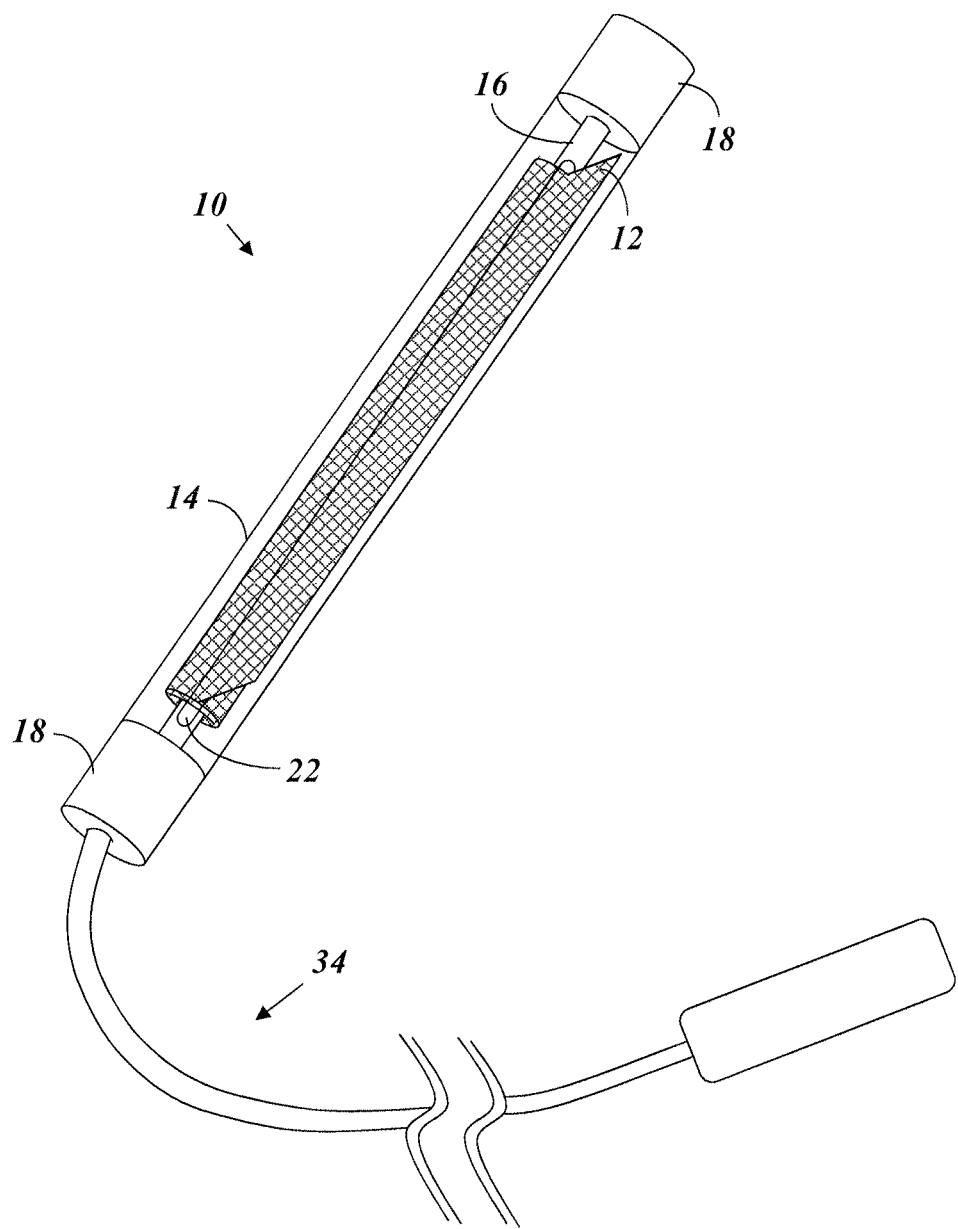
FIG. 9 is a perspective view of the deployment device of FIG. 3 with a positioning device coupled to one end of the deployment device, according to aspects of the present invention.

The deployment device 10 can be included with a wide variety of additional devices and/or apparatuses. For example, FIG. 9 depicts one example embodiment according to the present invention, in which the deployment device 10 is coupled at a distal end thereof to a positioning device 34. The position device 34 can be any suitable positioning device, including conventional graspers, articulation devices (e.g., adapted with rotational capability), and the like. The positioning device 34 can include a handle 36 and can be coupled to the deployment device 10 in any suitable way (e.g., can be screwed together, can be adhered together, can be coupled using mechanical fasteners, etc.). Like the deployment device 10, the positioning device 34 can be flexible, enabling the positioning device 34 to be utilized to advance the deployment device 10 through the intraperitoneal or other anatomical passageways and position the deployment device 10 once the target site has been reached. Upon reading the present specification, one of skill in the art will appreciate a wide variety of other devices and/or apparatuses that can be included with the deployment device 10. All such additional devices and/or apparatuses are contemplated within the scope of the present invention. The present invention is not limited to the specific implementations or intended applications (e.g., medical applications) described herein, which have been merely been described for purposes of illustration.

Although embodiments of the present invention have been described herein with reference to the mesh prosthesis 12 depicted in the figures, it should be appreciated that any suitable prosthesis (e.g., surgical fabric, film, and the like) can be utilized with the deployment device 10 described herein. The present invention is not limited to the specific example described herein of a mesh prosthesis 12. Rather, all suitable types of prostheses (e.g., sheet-like prostheses) are contemplated within the scope of the present invention.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A prosthesis deployment system, comprising:
an elongate housing extending along a longitudinal axis and comprising an exterior wall surrounding an interior cavity, the housing having a distal end and a proximal end;
an elongate opening formed in and completely through the exterior wall of the housing to the interior cavity;
a rotatable rod passing through the interior cavity of the housing and rotatably coupled to the housing; and
a prosthesis loaded on the rod in a rolled configuration around the rod in such a way that at least a portion of the prosthesis is configured to extend out of the elongate opening in the exterior wall of the housing;
wherein the prosthesis is deployed by being pulled through the elongate opening and unrolled from the rod; and
wherein the elongate housing, with the prosthesis loaded on the rod positioned within the interior cavity, prior to deployment has a bending stiffness of at most about 0.87 N/mm.

2. The system of claim 1, wherein the housing has an outer diameter of about 5 mm to about 10 mm and the bending stiffness of the deployment system is about 0.05 N/mm to about 0.87 N/mm.

3. The system of claim 1, wherein the housing has an outer diameter of about 3 mm.

4. The system of claim 1, wherein rotation of the rod in a loaded configuration deploys the prosthesis.

5. The system of claim 1, wherein rotation of the rod in a loaded configuration provides deployment of the prosthesis in a segment-by-segment, piecewise manner.

6. The system of claim 1, wherein the rod in a loaded configuration rotates at a manually determined rate in either rotational direction relative to the housing during manual deployment.

7. The system of claim 1, wherein the rod is completely contained within the housing.

8. The system of claim 1, wherein the proximal end of the housing is operationally coupled to a positioning device.

9. The system of claim 1, further wherein the housing and the rod are substantially the same length.

10. The system of claim 1, further comprising an elongate slot formed in the rod enabling the rod to receive the prosthesis, the elongate slot of the rod being substantially parallel to the elongate opening of the housing.

11. A prosthesis deployment kit, comprising:
a prosthesis; and
a deployment device, comprising:
an elongate housing extending along a longitudinal axis and comprising an exterior wall surrounding an interior cavity, the housing having a distal end and a proximal end;
an elongate opening formed in and completely through the exterior wall of the housing to the interior cavity; and
a rotatable rod passing through the interior cavity of the housing and rotatably coupled to the housing;
wherein the prosthesis is deployed from a rolled configuration on the rod by being pulled through the elongate opening and unrolled from the rod; and
wherein the deployment device has a bending stiffness of at most about 0.87 N/mm when the prosthesis is loaded on the rod in the rolled configuration.

12. A prosthesis deployment system, comprising:
an elongate housing extending along a longitudinal axis and comprising an exterior wall surrounding an interior cavity, the housing having a distal end and a proximal end;
an elongate slit opening formed in and completely through the exterior wall of the housing to the interior cavity; and
a rotatable rod passing through the interior cavity of the housing and rotatably coupled to the housing, wherein the rod is configured for loading a prosthesis on the rod in a rolled configuration around the rod in such a way that at least a portion of the prosthesis is configured to extend out of the elongate slit opening in the exterior wall of the housing;
wherein the prosthesis is deployable from the rod by being pulled through the elongate slit opening so as to unroll from the rod; and
wherein the deployment system, when the prosthesis is loaded on the rod prior to deployment, has a bending stiffness of at about 0.05 N/mm to about 0.87 N/mm.

* * * * *